(12) United States Patent
Bugler et al.

(10) Patent No.: US 10,196,671 B2
(45) Date of Patent: Feb. 5, 2019

(54) ASSAY METHOD FOR THE DETECTION OF VIABLE MICROBIAL CELLS IN A SAMPLE

(71) Applicant: 3M INNOVATIVE PROPERTIES COMPANY, St. Paul, MN (US)

(72) Inventors: Gerald J. Bugler, Mid Glamorgan (GB); Catherine M. Ramsay, Vale of Glamorgan (GB); Wililam J. Simpson, Wiltshire (GB); Mark B. Driscoll, Pontypridd (GB)

(73) Assignee: 3M Innovative Properties Company, St. Paul, MN (US)

( * ) Notice: Subject to any disclaimer, the term of this patent is extended or adjusted under 35 U.S.C. 154(b) by 1286 days.

(21) Appl. No.: 13/737,119

(22) Filed: Jan. 9, 2013

(65) Prior Publication Data

US 2013/0189717 A1     Jul. 25, 2013

Related U.S. Application Data

(62) Division of application No. 12/375,724, filed as application No. PCT/GB2007/002923 on Aug. 1, 2007, now abandoned.

(30) Foreign Application Priority Data

Aug. 1, 2006  (GB) .................................. 0615302.7

(51) Int. Cl.
   *C12Q 1/66*   (2006.01)
   *C12Q 1/06*   (2006.01)

(52) U.S. Cl.
   CPC ................. *C12Q 1/66* (2013.01); *C12Q 1/06* (2013.01)

(58) Field of Classification Search
   CPC ...................................................... C12Q 1/06
   See application file for complete search history.

(56) References Cited

U.S. PATENT DOCUMENTS

| | | | |
|---|---|---|---|
| 3,408,440 A | 10/1968 | Voss | 436/543 |
| 3,745,090 A | 7/1973 | Chappelle et al. | 195/103 |
| 4,014,745 A * | 3/1977 | Fletcher | C12Q 1/18 435/259 |
| 4,303,752 A * | 12/1981 | Kolehmainen | C12Q 1/008 435/18 |
| 5,004,684 A | 4/1991 | Simpson et al. | 435/8 |

FOREIGN PATENT DOCUMENTS

| | | | |
|---|---|---|---|
| CH | 678 065 | 7/2001 | ............ C12Q 1/00 |
| CN | 1680804 | 10/2005 | ............ C12N 1/20 |
| EP | 1 134 291 | 9/2001 | ............ C12Q 1/66 |

OTHER PUBLICATIONS

Chung, Y. et al.; "ATP as a measure of anaerobic sludge digester activity";Journal Water Pollution Control Federation; vol. 60, No. 1; 1988; pp. 107-111.
Gomori, G.; "[16] Preparation of Buffers for Use in Enzyme Studies"; Methods in Enzymology; vol. 1; 1955; pp. 138-146.
Karamohamed, S. et al.; Research Report entitled "Bioluminometric Method for Real-Time Detection of ATPase Activity"; BioTechniques; vol. 31, No. 2 (2001); pp. 420-425.
Mannazzu, I. et al.; "Vanadate and copper induce overlapping oxidative stress responses in the vanadate-tolerant yest *Hansenula polymorpha*"; Biochimica et Biophysica Acta; vol. 1475; No. 2; 2000; pp. 151-156.
Maturana, H. et al.; "Poly(N-vinylpyrrolidone) as metal ion liquid-liquid extractant"; Polymer Bulletin; vol. 45; 2000; pp. 425-429.

* cited by examiner

*Primary Examiner* — Bin Shen
(74) *Attorney, Agent, or Firm* — Eric E. Silverman

(57) ABSTRACT

The present invention discloses an assay method for the detection of viable microbial cells in a sample, the assay method comprising the steps of: i) adding an ATP degrading enzyme to a sample suspected of containing viable microbial cells to substantially degrade any extracellular ATP in the sample; ii) adding a phosphate containing compound to the sample to substantially halt action of the ATP degrading enzyme; and iii) subjecting the sample to a detection assay to establish the level of undegraded ATP in the sample to provide an indication of the level of viable microbial cells in the sample.

16 Claims, 10 Drawing Sheets

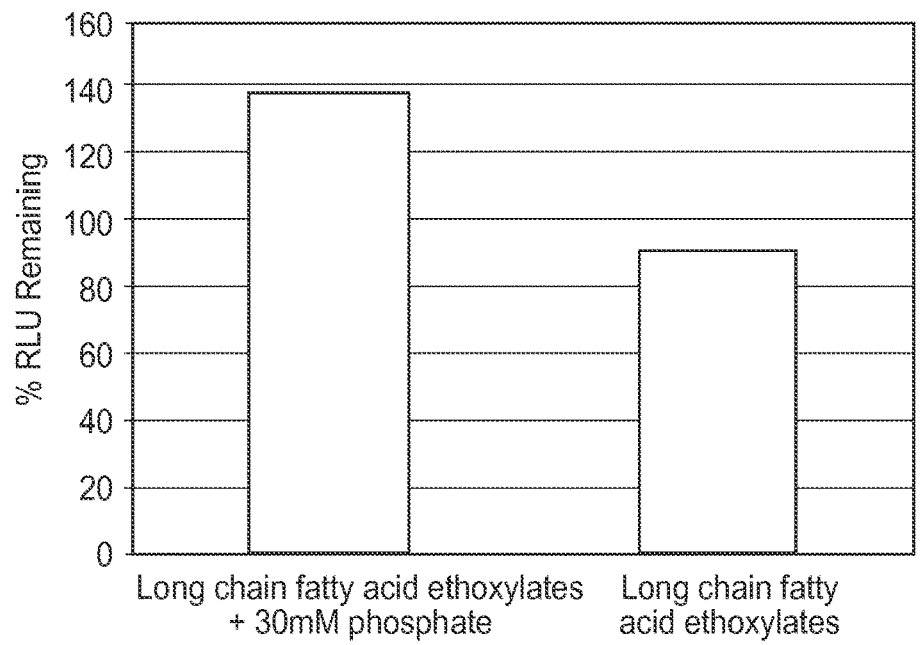
FIG. 1.1
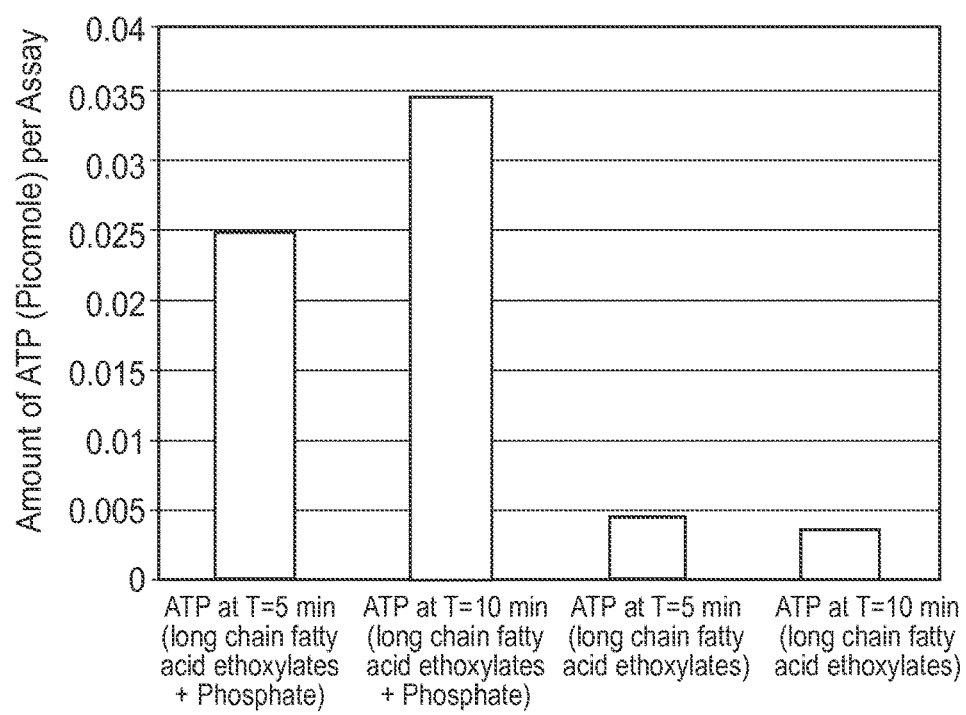
FIG. 1.2

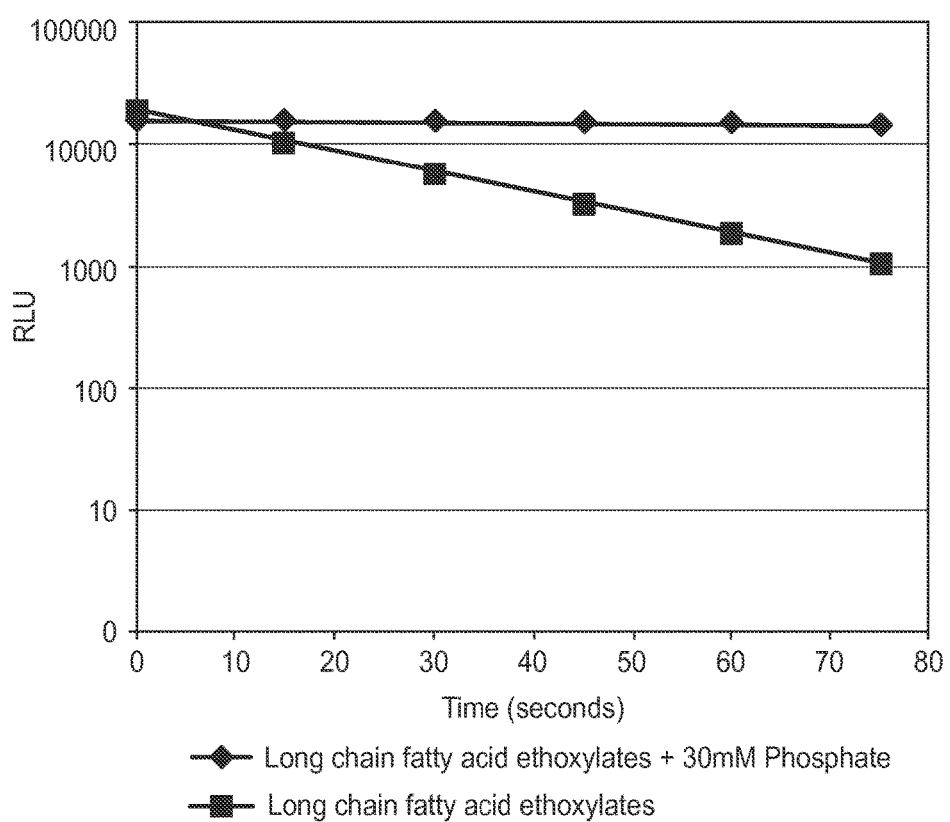
FIG. 1.3

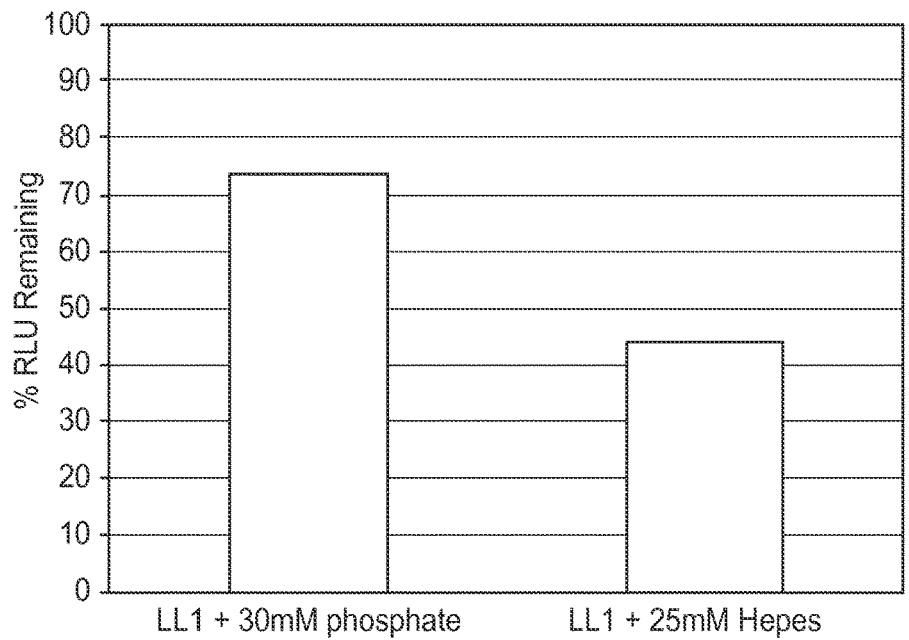
FIG. 2.1
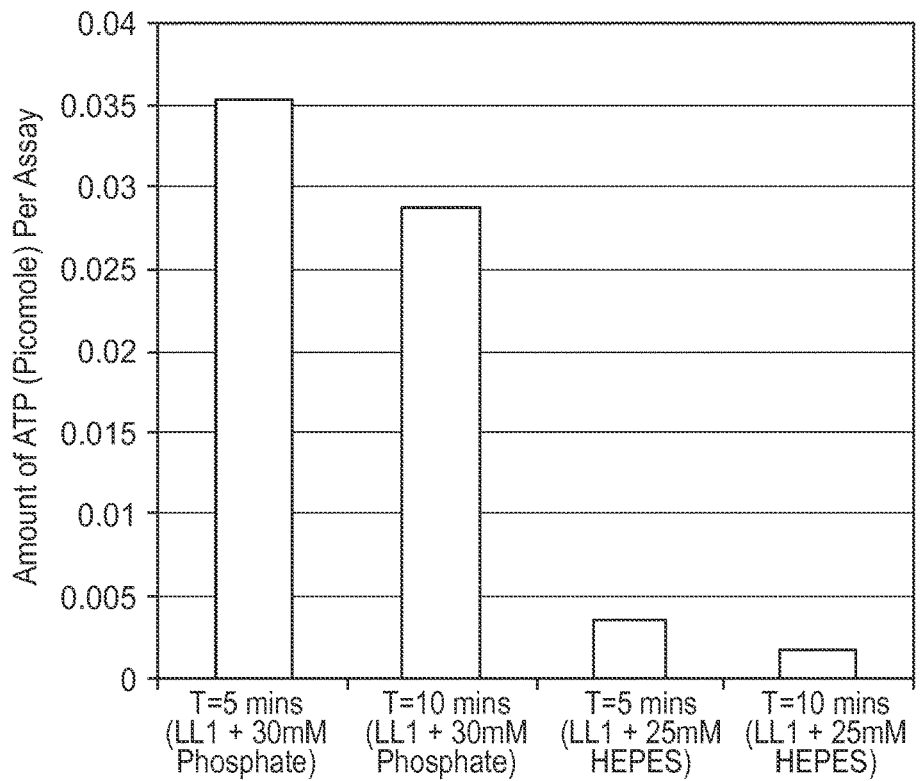
FIG. 2.2

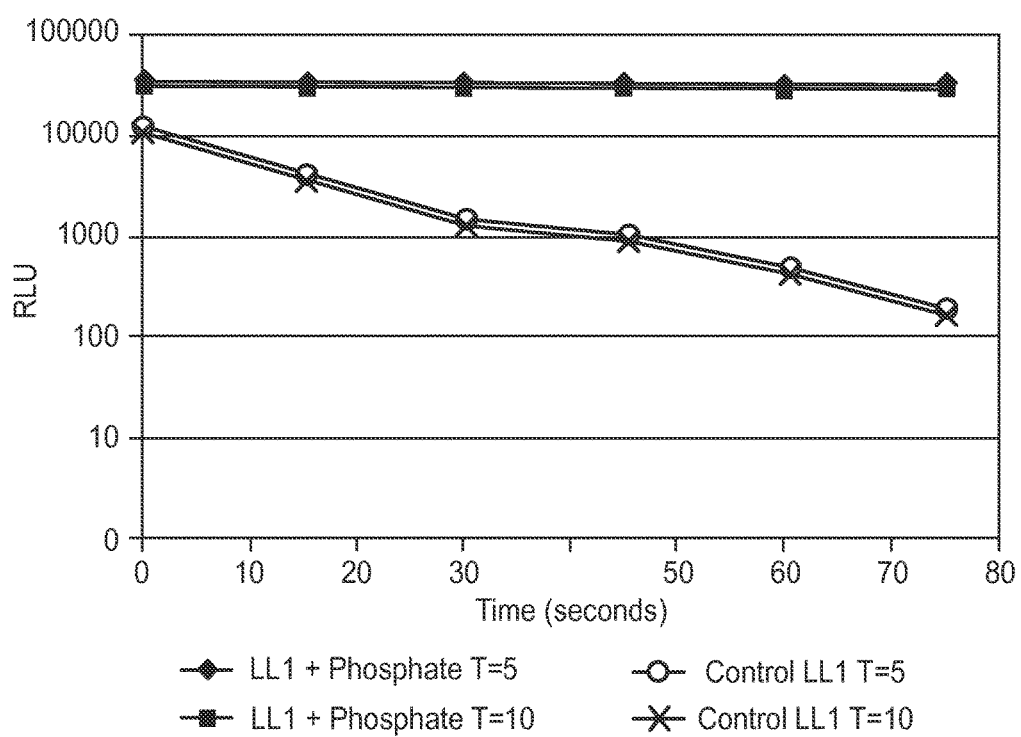
FIG. 2.3

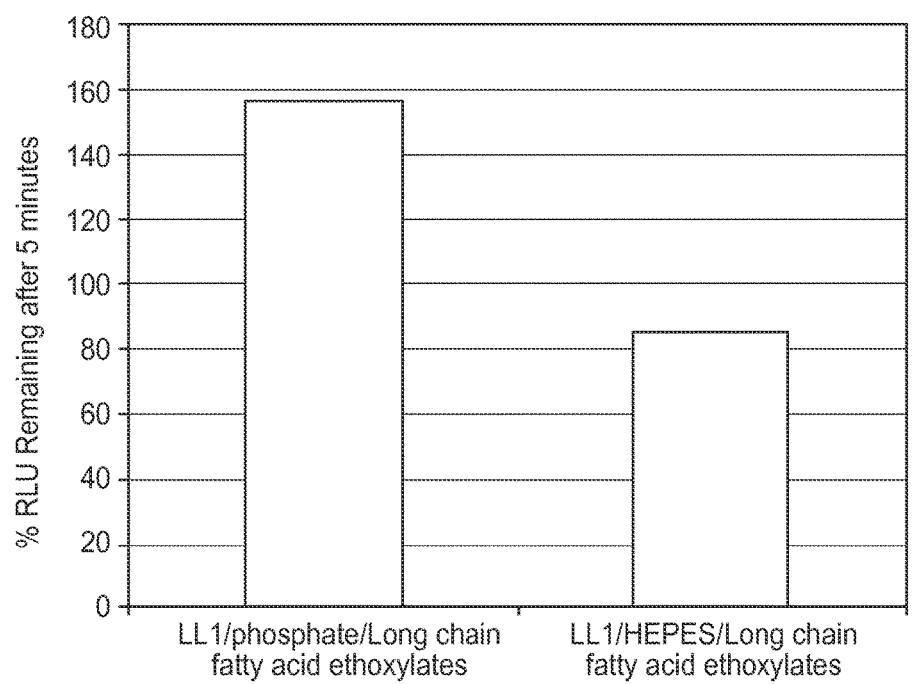
FIG. 3.1

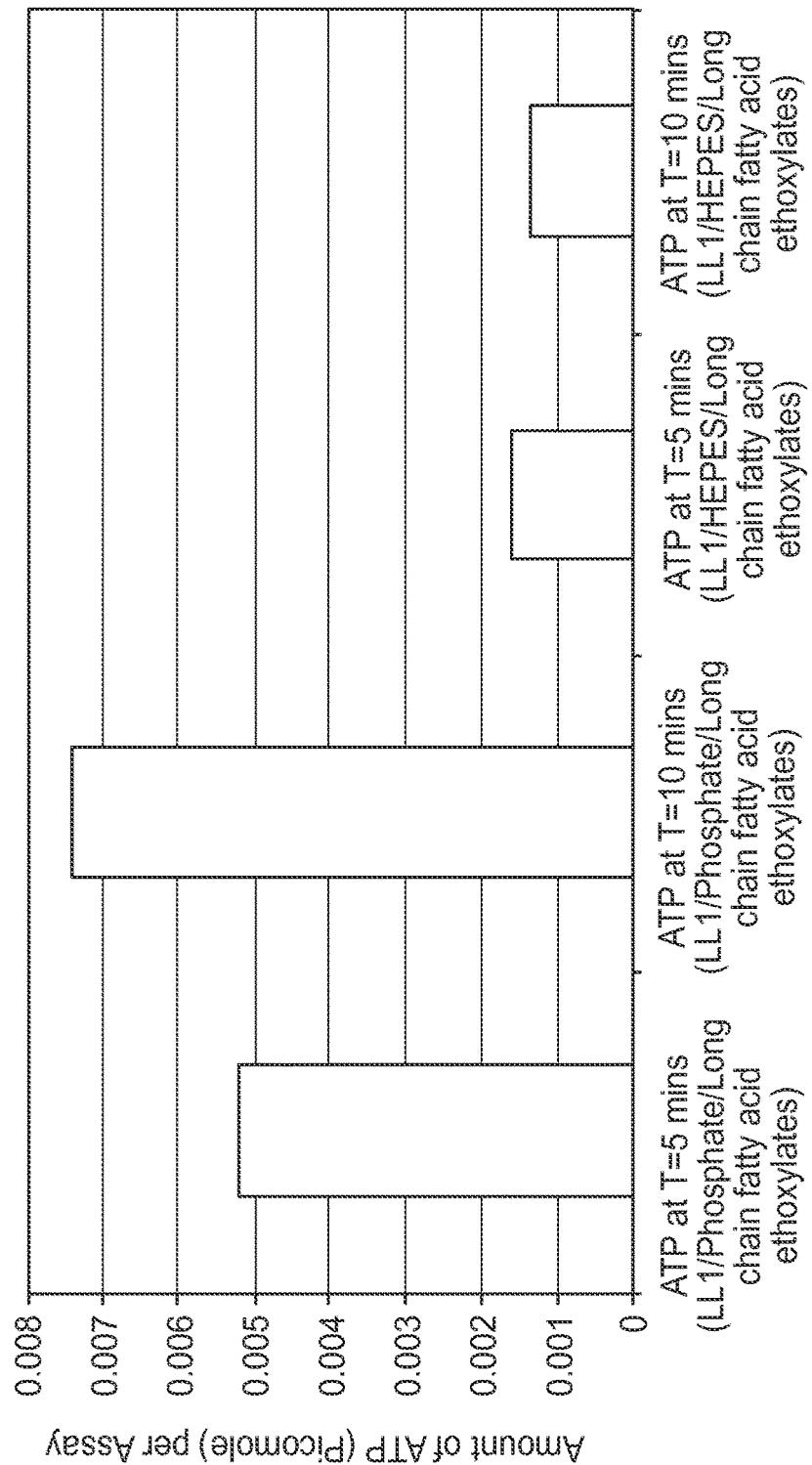
FIG. 3.2

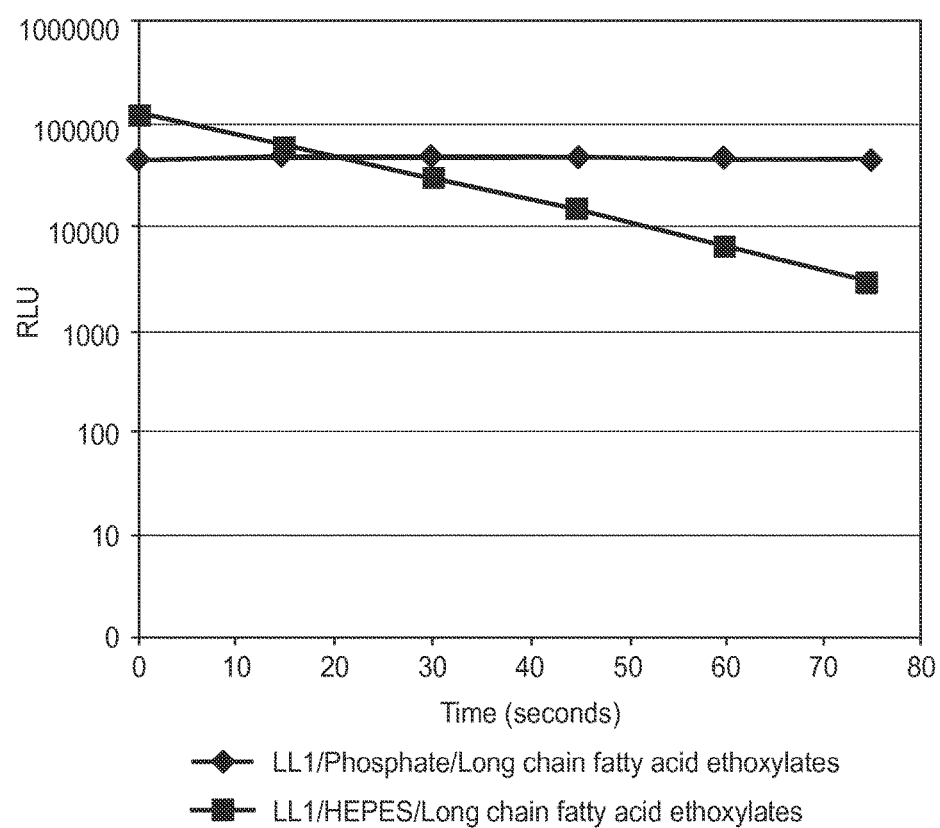
FIG. 3.3

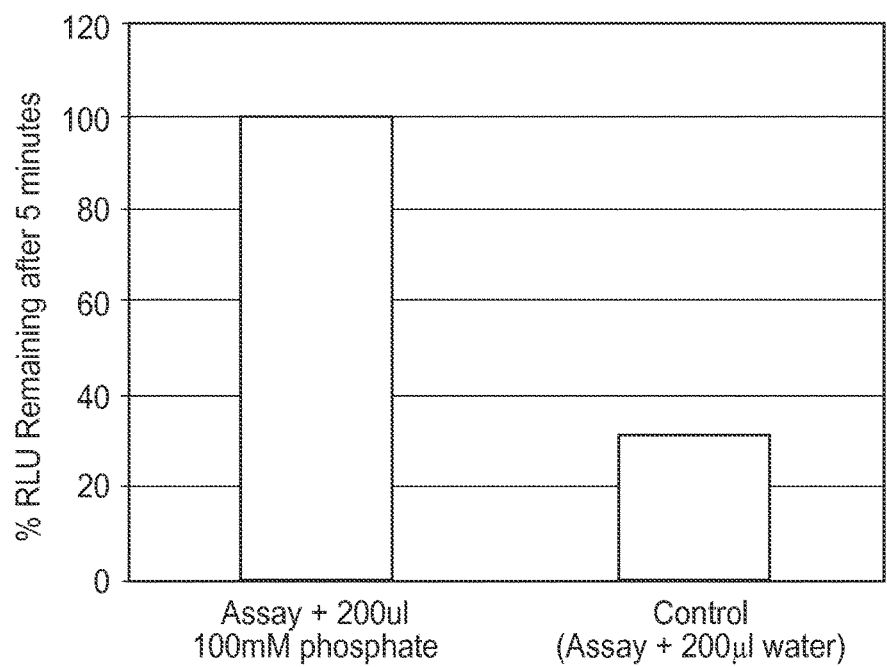
FIG. 4.1

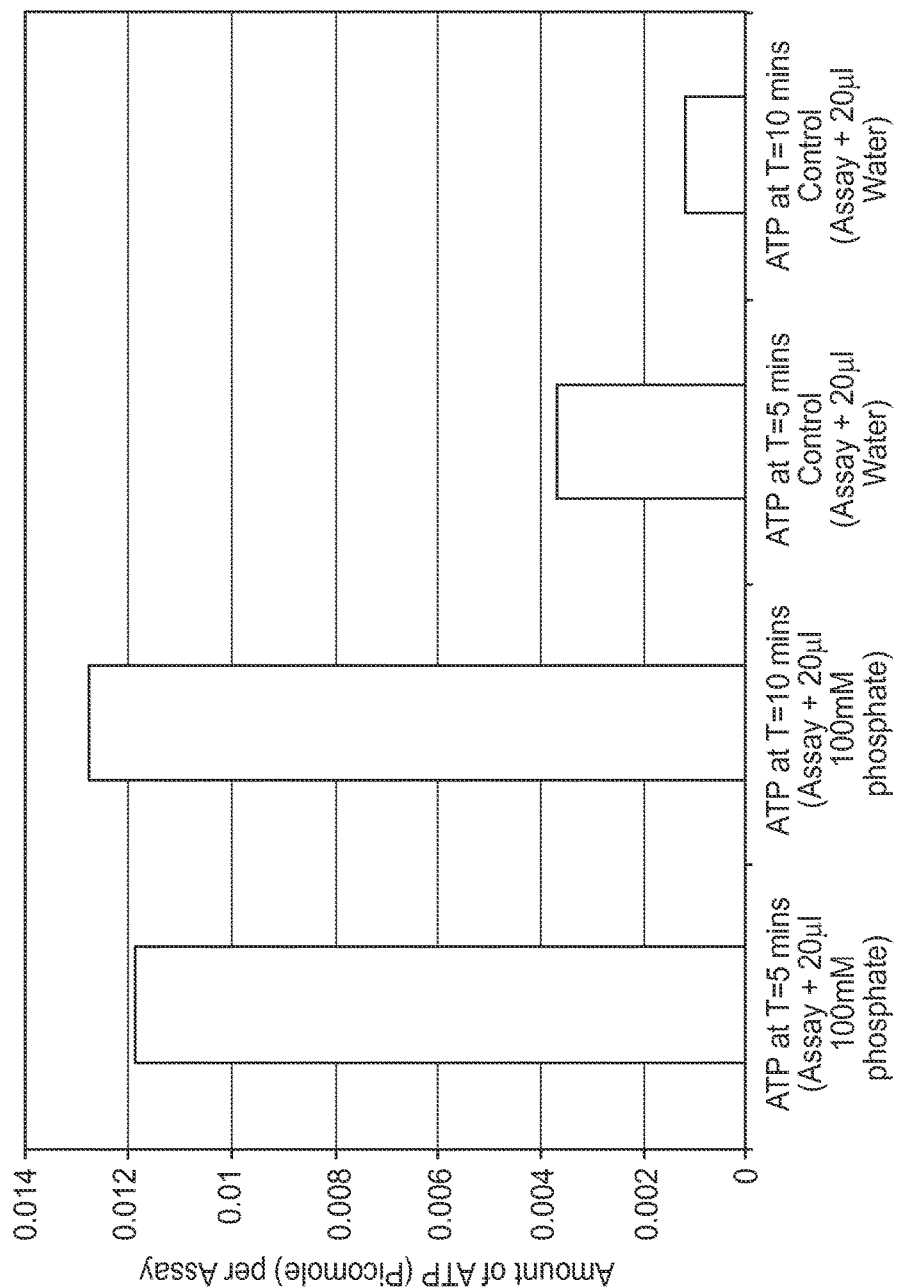
FIG. 4.2

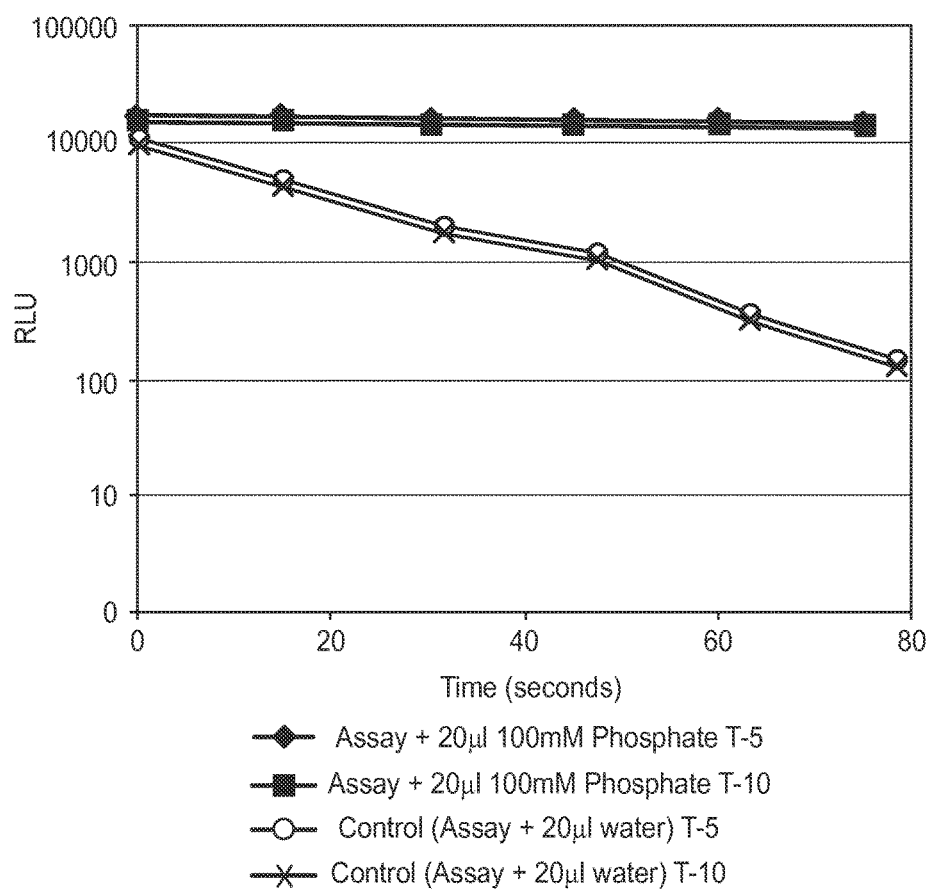
FIG. 4.3

ASSAY METHOD FOR THE DETECTION OF VIABLE MICROBIAL CELLS IN A SAMPLE

CROSS REFERENCE TO RELATED APPLICATIONS

This application is a division of U.S. patent application Ser. No. 12/375,724, filed Dec. 17, 2009, which is a national stage filing under 35 U.S.C. 371 of PCT/GB2007/002923, filed Aug. 1, 2007, which claims priority to United Kingdom Application No. 0615302.7, filed Aug. 1, 2006, the disclosure of which is incorporated by reference in its entirety herein.

Microbial contamination of samples, such as samples obtained from humans, food samples or the environment, may be due to a number of different types of microorganisms. The microorganisms may be present as either single colonies or multiple types of microbe colonies and for example, bacteria and fungi may be present in equal or differing amounts in or on the sample to be tested.

Current methods of detection of microbial contamination involve the detection of Adenosine triphosphate, from hereon referred to as ATP, as this is present in all living matter. The presence of ATP in living material means that this compound provides a good indicator of the presence of life-forms such as microorganisms.

One of the most commonly used methods for the quantitative detection of ATP is the reaction of the compound with firefly luciferase. The firefly luciferase reaction for ATP employs a purified enzyme (firefly luciferase), a substrate (D-luciferin), magnesium ions and oxygen. Light produced through the reaction of ATP with D-luciferin and oxygen is measured with a luminometer. Under appropriate conditions, the intensity of light produced by the reaction is proportional to the amount of ATP present in the sample. The light produced in the reaction is emitted as a continuous glow which makes the assay more reliable, as it reduces the reliance on precise timing to view a result on the part of the analyst.

When measuring samples including live microorganisms, (which are also referred to as viable cell biomass or viable microbial cells), there are other cells, and organic material present in the sample as contaminants This additional organic material, which also includes ATP, is also detected by known assay methods, including the firefly luciferase reaction. If this "extracellular" ATP, which is present as a result of contaminants in the sample, is also detected, this can result in an incorrect measurement of the level of viable cell biomass in the sample. This is because ATP from the contaminants is detected as well as the ATP from the viable microorganisms. It is the fact that levels of extracellular ATP are detected which can give a false indication of the level of viable cell biomass due to a higher than expected reading. This is very undesirable when testing food samples, for example, or products to be used in healthcare, where strict limits are imposed on the levels of microbes that can be present on an item if it is to be used. If these limits are exceeded, the item has to be discarded, which leads to a high level of wastage and costs. Because known assays detect extracellular material, a false indication of the viable cell biomass is often given and hence is a severe limitation of known assays. Products such as healthcare items may be thrown away when they need not be because in fact, if correct measurement was given, the actual viable cell biomass is within desirable limits. Therefore an efficient method of removal of ATP not attributable to viable biomass is desirable.

Methods have been developed to remove ATP from a sample. When assessing the amount of viable cell biomass present in a sample (for example in a food sample, in cooling tower water samples, or in effluent samples), it is usual to remove the ATP located outside the living microbial cells (extracellular or extraneous ATP) prior to extracting ATP from the microbial cells. This step allows the ATP within those microbial cells to be discriminated from the large amounts of extracellular or extraneous ATP that is associated with the organic material in a sample and the non-microbial cells (so called 'somatic' cells) originating from the organic matter in the food sample or other types of sample being assayed.

ATP degrading enzymes are known to be used to remove extracellular ATP prior to extraction of cellular ATP. Suitable enzymes used include ecto—ATPases among others and specifically apyrases. Apyrases are enzymes that catalyse the hydrolysis of ATP, producing adenosine diphosphate (ADP) and inorganic phosphate. In a second step they can further degrade ADP to adenosine monophosphate (AMP) and inorganic phosphate. For optimum activity, they require divalent cations, such as calcium or magnesium.

Apyrases can be obtained from a range of sources including potatoes, peas, and bacteria. Apyrases from a variety of sources display a large degree of homology, particularly in relation to the active site of the enzyme.

Apyrases obtained from potatoes have been widely exploited for removal of extracellular ATP prior to assay of microbial ATP using the firefly luciferase reaction. A method of detecting and counting bacteria in body fluids has been discussed in U.S. Pat. No. 3,745,090. Further, potato apyrase has featured in many assays for live microbial cells in, for example water, beer, soft drinks, wine, foodstuffs and in a variety of other products.

However, there are three main problems usually associated with methods to remove ATP from samples and in particular with the use of apyrases to remove ATP that is not associated with microbial cells.

Firstly, the removal of ATP by apyrase is not a rapid process. Typically it is the slowest step in the entire biomass estimation procedure which is not desirable with high throughput sampling. While the extraction and ATP measurement steps can be carried out within a timeframe of seconds, removal of extracellular ATP using apyrase requires a timescale of minutes. Treatment periods in the range 5-30 minutes are typical.

Attempts have been made to overcome the difficulties associated with the speed of ATP removal by apyrase through use of longer reaction times and elevated temperatures. For example, some commercially-available biomass assay kits based on ATP detection employ a 15 minute apyrase treatment step and advise that a temperature in excess of room temperature is employed to speed the reaction. However, the assays are still too slow for high throughput assays and additionally require a heating source.

Assay protocols have been devised in which apyrase is immobilized on a solid support to provide a localized concentration of enzyme which allows the contact time between apyrase and extracellular ATP to be reduced. Even so, several minutes are still required for removal of ATP. Further, increasing the concentration of enzyme can contribute to an additional problem, in that there may be residual apyrase activity during the extraction step. This leads to sample instability, making the overall assay both time-sensitive and operator-dependent. A complementary strategy may be to use additional enzymes to assist in destruction of ATP by apyrase. Such enzymes can include adenosine phosphate deaminase, hexokinase and adenosine triphosphatase. However, this additional step can increase assay times, and increase the cost of performing the assay as additional reagents are used.

A second problem associated with known techniques is that the ability of apyrase to remove ATP from test samples is often less than that seen in the case of model solutions. This is due to the presence of materials in test samples which inhibit the activity of apyrase.

Several strategies have been used to deal with the fact the some samples inhibit apyrase activity. For example, attempts have been made to remove sample residues from the assay matrix by trapping yeast or bacteria present in the sample on membrane filters prior to washing the filters with an ATP-free buffer solution. This is useful to a degree in the case of filterable beverages such as beer, wine and soft drinks. However it is difficult, and sometimes impossible, to apply in the case of products that cannot be filtered without the use of additional treatments to increase product filterability for example, the use of proteolytic enzymes and high temperatures. Examples of products which present difficulties in filtration include milk and related dairy products, and fruit juice and related products. Further some food and drink samples (for example beer, wine and soft drinks) inhibit the activity of apyrase due to the low pH values of such products.

Third, residual apyrase activity remaining at the time of extraction from live cells can degrade some of the ATP released from cells. This can cause the underestimation of the numbers of live cells present in the sample.

Attempts have been made to employ inhibitors of apyrase activity to prevent such loss of ATP. Sodium ortho-vanadate has been used to inhibit apyrase activity when measuring concentrations of extracellular ATP remaining after apyrase treatment of beer samples and prior to ATP extraction. However, ortho-vanadate has drawbacks in that it is highly toxic to both users and the microbial cells that are being assayed, so false readings can result.

Gadolinium has been shown to inhibit apyrase activity. However, this element has antimicrobial properties and is thus unsuitable for inhibiting potato apyrase in microbiological tests.

Other compounds which have been considered and rejected for use in ATP assays to inhibit apyrase activity prior to ATP extraction include but are not limited to: sodium deoxycholate, sodium fluoride, sodium azide, and various other small molecule inhibitors. While some of these materials are relatively good inhibitors of apyrase, all suffer from drawbacks with respect to their use in tests for live microorganisms. Some are inhibitory to microbial cell metabolism; some are hazardous to users; while others strongly inhibit the activity of firefly luciferase. Proteolytic enzymes, including trypsin, chymotrypsin, subtilisin, proteinase K and papain have also been used.

Attempts have also been made to inactivate apyrase simultaneous to the extraction process, for example using perchloric acid extraction. Such extraction methods are very aggressive and apyrase is destroyed when it comes into contact with the extraction agent. However, because of their inhibitory effects on firefly luciferase, extracts produced with such extractants have to be diluted substantially prior to testing, which can also result in false readings.

SUMMARY OF THE INVENTION

The invention relates to an assay method for the detection of viable microbial cells in a sample. In particular, but not exclusively, the invention relates to the assessment of the cleanliness of surfaces and the accurate measurement of the numbers of live microorganisms (viable microbial cells/viable cell biomass and which forms are interchangeable) in various types of samples including solids, liquids and gases. The term microorganism includes bacteria, yeasts, fungi or algal blooms.

The present invention provides an assay with apyrase inhibitors that:
i) are effective in the inhibition of apyrase activity;
ii) have a low risk of toxicity, carcinogenicity and teratogenotoxicity to users of the material carrying out ATP assays;
iii) are non-toxic to microbial cells, having no effect on ATP pool levels—this is necessary as the inhibitor of apyrase must be present in the assay prior to extraction of ATP from live cells.
iv) are not so inhibitory to luciferase activity that the subsequent assay becomes unworkable.

The present invention provides a quick, efficient and accurate indication of the level of viable microbial cells in a sample.

It has been found that there is a need to combine optimum ecto-ATPase action to remove extracellular ATP, together with the precise switching off of the ecto-ATPase action, when extracellular ATP has been removed. Optimum ecto-ATPase action prevents damage of viable microorganisms while allowing an accurate quantitative analysis of the microorganisms.

It has been found unexpectedly that phosphorous-containing materials inhibit apyrase activity Inhibition of apyrase activity by the phosphorous/phosphate containing materials is unexpected because assays involving the use of apyrase have traditionally used the detection of phosphate production as the measure of activity of the enzyme. This has essentially precluded the use of phosphorous-containing buffers or compounds in the test solution in order to avoid assay interference.

According to a first aspect of the invention there is provided an assay method for the detection of viable microbial cells in a sample, the assay method comprising the steps of:
i) adding an ATP degrading enzyme to a sample suspected of containing viable microbial cells to substantially degrade any extracellular ATP in the sample;
ii) adding a phosphate containing compound to the sample to substantially halt action of the ATP degrading enzyme; and
iii) subjecting the sample to an assay to establish the level of undegraded ATP in the sample to provide an indication of the level of viable microbial cells in the sample.

In one embodiment the method includes the step of first isolating a sample suspected of containing viable microbial cells having intracellular ATP and extraneous material having extracellular ATP.

Preferably, an extractant is added to the sample prior to assaying the level of undegraded ATP in order to extract undegraded ATP from the sample.

Preferably, the ATP degrading enzyme is an ecto-ATPase.

It is preferred that the ecto-ATPase is an apyrase.

In most embodiments the ATP degrading enzyme such as the apyrase is buffered. Preferably, the apyrase reagent is buffered to have a pH value of substantially 6.5. Standard buffers may be used such as HEPES Buffer. The pH may be in the range of 20 substantially 9 to 5, 8 to 6 or 7.5 to 6.2.

It is preferred that the apyrase is of a concentration in the range of 1 ml apyrase to 10µ, of $10^{-7}$M of ATP.

The apyrase reaction is typically carried out at room temperature and a typical reaction time is 1-30 minutes, more typically 15 minutes.

Preferably divalent cations are added to a reagent including the apyrase. It is preferred that the divalent cations are calcium ions and/or magnesium ions. The addition of divalent cations is beneficial because apyrase has low activity in the presence of substances which can bind to divalent cations since it requires calcium ions (or other divalent cations) for maximum activity. Typically a solution of Magnesium Chloride is used at a typical concentration of 5 mM.

It is preferred that the phosphate containing compound is selected from one or more of sodium phosphate, potassium phosphate, sodium pyrophosphate, penta-sodium triphosphate or sodium polyphosphate.

It is envisaged that the extractant is a surface-active agent that is used to extract ATP from live cells.

It is preferred that the surface-active agents include one or more of quaternary ammonium compounds, dialkyl ammonium salts and bis-biguanides.

More preferably, the extractant is selected from one or more of the group consisting of N-N-dimethyldodecan-1-amine (GENAMIN), chloroprozamine, liquid lysate (LL1), dichlorogallium (III)$^\beta$-diketonato derivatives GaCl$_2$ (BDK) and combinations thereof. These are only illustrations of the extractants used and are not intended to be limiting.

Typically the extractants are used at a concentration of 0.05-50 g/l and more typically 0.1-5 g/l.

It is envisaged that the extractant period is carried out 3-10 minutes, more typically 4-8 minutes and most preferably for a period of substantially 5 minutes.

Typically, the ATP is extracted at room temperature, which reduces the risk of viable cells being killed by elevated temperatures.

In most embodiments, one or more neutralizing agents are added to the sample containing the extractant. This has the benefit, in particular with surface-active agents, of inactivating the reagents so they do not have a destructive effect on the viable microorganisms in the sample.

Preferably, the assay is a light emitting assay.

It is preferred that light emitting assay to monitor the levels of ATP is a luciferase assay.

In a preferred method, phosphate-containing materials in the sample are precipitated prior to performing the apyrase reaction.

Alternatively, the residual activity of apyrase in assays for viable microbial cells is inhibited by incorporating the one or more phosphate-containing substances in a reagent which is added to the sample matrix after the apyrase treatment step.

In most embodiments a second reagent is added to the sample. A second reagent is added that is designed to increase intracellular ATP levels by manipulation of cellular metabolism, an ATP extraction reagent, or an ATP detection reagent containing luciferase and luciferin. These are illustrative of the materials that can be used and are not intended to be limiting.

According to a second aspect of the invention there is provided an assay kit for the detection of viable microbial cells in a sample, the assay kit including a container including an ATP degrading enzyme, a container with a phosphate containing compound together with means to combine the enzyme and phosphate containing compound to carry out an assay method comprising the steps of:

i) adding an ATP degrading enzyme to a sample suspected of containing viable microbial cells to substantially degrade any extracellular ATP in the sample;

ii) adding the phosphate containing compound to the sample to substantially halt action of the ATP degrading enzyme;

iii) allowing the phosphate containing compound to react with the ATP degrading enzyme; and iv) subjecting the sample to a detection assay to establish the level of undegraded ATP in the sample to provide an indication of the level of viable microbial cells in the sample.

Preferably, the assay kit includes an extractant to be added to the sample prior to assaying the level of undegraded ATP to extract the undegraded ATP from the sample.

It is preferred that the ATP degrading enzyme is an ecto-ATPase. Typically, the ecto-ATPase is an apyrase.

Preferably that the ATP degrading enzyme such as the apyrase is provided as a buffered solution at a pH value repeat range of substantially 6.5.

It is preferred that the apyrase is of a concentration in the range of 1 ml apyrase to 10 µl of $10^{-7}$M of ATP. A typical value is 0.96 units per ml. However, as reactions are strongly influenced by the composition used and reaction temperatures, an appropriate amount of apyrase can be adjusted for a particular reaction.

Preferably divalent cations are included in a reagent including the apyrase.

It is preferred that the divalent cations are calcium ions and/or magnesium ions at a typical concentration of 5 mM.

It is preferred that the phosphate containing compound is selected from one or more of sodium phosphate, potassium phosphate, sodium pyrophosphate, penta-sodium triphosphate or sodium polyphosphate.

The extractant can be a surface-active agent that is used to extract ATP from live cells. It is preferred that the surface-active agents include one or more of quaternary ammonium compounds, dialkyl ammonium salts and bis-biguanides. More preferably, the extractant is selected from one or more or the group consisting for example of N-Ndimethyldodecan-1-amine (GENAMIN), chloroprozamine, liquid lysate (LL1), dichlorogallium(III)$^\beta$-diketonato derivatives GaCl$_2$ (BDK.).

Typically the extractants are used at a concentration of 0.05-5 g/l more typically 0.1-5 g/l.

In most embodiments, the assay kit includes neutralizing agents which are added to the sample containing the extractant.

An embodiment of the invention will now be described by way of example only with reference to the accompanying Figures and experiments in which:

FIGS. 1.1, 2.1, 3.1 and 4.1 show the Relative Light Units (RLU) provided by samples using different extractants, one sample having had a phosphate compound added, and the other sample being a control in which phosphate has not been added;

FIGS. 1.2, 2.2, 3.2 and 4.2 show the amount of ATP released from samples using different extractants both with and without phosphate included after 5 and 10 minutes; and FIGS. 1.3, 2.3, 3.3 and 4.3 show the light emitted by samples containing various extractants with and without phosphate over a period of 70-80 seconds.

The above Figures relate to the following experimental data, derived from experiments 1 to 4. Each experiment will now be described in turn.

EXPERIMENT 1

Method 1.1. *Leuconostoc* sp MD 110 was grown by streaking a bead onto Tryptone Soya Broth agar to revive bead for stock (place in 30° C. incubator overnight)

1.2. A loop was taken from this plate and transferred to 10 ml Tryptone Soya Broth and grown at 30° C. for exactly 40 hours.

1.3. Once cloudy, indicating that the cells were in early stationary phase, the culture was placed in a place in fridge for 2 hours. Cells were washed twice in ice-cold Reverse Osmosis water in centrifuge (4500 rpm for 10 mins), resuspended in 10 ml cold Reverse Osmosis water and stored in the fridge.

1.4. Cells for the experiment were prepared using a 100× dilution of this stock with a sterile solution of glucose (10 g/l) and $MgCl_2$ (5 mM) at room temperature. Cells were diluted into this solution at least 20 minutes prior to starting each experiment to allow adaptation to the new conditions. The glucose provides energy for the cells, and the magnesium salt facilitates apyrase activity in the subsequent assays.

2. 1 ml of the above cell suspension was added to a cuvette.

3. The suspension was then treated with 1 ml of reconstituted apyrase 0.96 units per ml, and 10 μl of ATP ($10^{-7}$ M) was added and left for 15 minutes at room temperature.

4. 4×100 μl aliquots of the treated suspension was transferred to clean cuvettes.

5. To two of the cuvettes, 100 μl of sterile Reverse Osmosis water was added.

6. 100 μl of luciferase was then added to one of the water cuvettes and read in a luminometer.

7. 100 μl of a solution of long chain fatty acid ethoxylates (1 g/l) and 30 mM phosphate was added to each of remaining two cuvettes and a timer was started. The long chain fatty acid ethoxylates utilized in the examples 1 to 4 was N-N-dimethyldodecan-1-amine (GENAMIN).

8. Immediately, 100 μl of luciferase enzyme was added to one of the cuvette (a luciferase/luciferin reagent formulated with a detergent-resistant luciferase (Promega, Ultraglo) reconstituted with 17.5 ml of HEPES buffer) and read in a luminometer.

9. The cuvette was removed from the luminometer and 100 μl of $10^{-7}$M ATP was added to standardize with ATP.

10. The solution was read again in a luminometer and for five consecutive times in a row to check final kinetics of the reaction with the results being given as a measure of Relative Light Units (RLU).

11. After 5 minutes, steps 6-9 were repeated for the second cuvette.

12. For the control, steps 4-10 were repeated using a solution of long chain fatty acid ethoxylates (1 g/l) without phosphate.

FIG. 1.1 shows the percentage RLU remaining after 5 minutes extraction with each extractant. The assay that had 30 mM phosphate mixed with the extractant experienced a 38% rise in RLU from T-5 to T-10. In the assay that contained no phosphate there was a 9% reduction in RLU from T-5 to T-10.

The increase in RLU seen in the assay containing phosphate may be explained by the slow extraction time of a solution of long chain fatty acid ethoxylates. More ATP was being extracted over time, whilst the action of apyrase was reduced due to the presence of phosphate.

In the assay that did not contain any phosphate, it is theorized that the RLU level dropped because the apyrase was breaking down ATP more rapidly than it was being extracted by a solution of long chain fatty acid ethoxylates.

This also may explain the rise in the amount of ATP per assay in the assay containing phosphate and the drop in the amount of ATP assay in the assay without phosphate (FIG. 1.2).

It is clear from studying the kinetics of the 2 assays (FIG. 1.3) that 30 mM phosphate inhibits the action of apyrase, as the amount of ATP is not being degraded.

EXPERIMENT 2

Method

1. *Leuconostoc* sp MD 110 was grown by streaking a bead onto de Man Rogosa Sharpe agar to revive bead for stock (place in 30° C. incubator overnight).

a. A loop was taken from this plate and transferred to 10 ml Tryptone Soya Broth and grown at 30° C. for exactly 40 hours.

b. Once cloudy, indicating that the cells were in early stationary phase, the culture was placed in a place in fridge for 2 hours. Cells were washed twice in ice-cold Reverse Osmosis water in centrifuge (4500 rpm for 10 mins), resuspended in 10 ml cold Reverse Osmosis water and stored in the fridge. c. Cells for the experiment were prepared using a 100× dilution of this stock with a sterile solution of glucose (10 g/l) and $MgCl_2$ (5 mM) at room temperature. Cells were diluted into this solution at least 20 minutes prior to starting each experiment to allow adaptation to the new conditions.

d. A luciferase/luciferin reagent formulated with a detergent-resistant luciferase (Promega, Ultraglo) (Liquid Lysate) enzyme was reconstituted in 17.5 ml phosphate buffer pH 7.75.

2. 1 ml of the above cell suspension was added to a cuvette.

3. The suspension was then treated with 1 ml of reconstituted apyrase 0.96 units per ml, and 100 of ATP ($10^{-7}$M) was added and left for 15 minutes at room temperature.

4. Two 100 μl aliquots of the treated suspension was transferred to clean cuvettes.

5. 100 μl of the luciferase/luciferin reagent formulated with a detergent-resistant luciferase (Promega, Ultraglo)/phosphate luciferase was added to each of the cuvettes.

6. To the remaining 2 cuvettes 100 μl of a solution of long chain fatty acid ethoxylates (the extractant) was added and a timer started.

7. Cuvette 1 was read in a luminometer after 5 minutes extraction time.

8. Cuvette 1 was removed from the luminometer and 10 μl of $10^{-7}$M ATP was added to standardise.

9. The sample was returned to the luminometer and read again, then read 5 consecutive times in a row in order to determine the final kinetics of the reaction.

10. After a further five minutes steps 9-11 were repeated for cuvette 2.

11. For the control steps 4 to 13 were repeated but using a luciferase/luciferin reagent formulated with a detergent-resistant luciferase (Promega, Ultraglo) reconstituted in 25 mM HEPES buffer pH 7.75.

As shown in FIG. 2.1, in the assay that contained the phosphate, 73.7% of the RLU produced after 5 minutes extraction still remained at T=10 minutes.

In the assay that did not contain phosphate only 43.5% of the RLU signal produced after 5 minutes remained at 10 minutes.

It is difficult to directly compare the two different assays based on the amount of ATP present at each time point (FIG. 2.2). The assay containing phosphate has a much greater amount of ATP remaining at T=10 than the control assay (0.029 picomoles compared to 0.00163 picomoles). However, assay one had much more ATP at T=5 than the control assay (0.035 picomoles compared to 0.00163 picomoles).

The effectiveness of phosphate in inhibiting apyrase is indicated by the percentage of ATP remaining at T=10 compared to how much was present at T=5. Thus, for assay one the amount of ATP at T=10 is 81.3% of that present at T=5. For the control assay the amount of ATP at T=10 is 47% of that present at T=5.

The kinetics of the two assays (FIG. 2.3) provide clear evidence of phosphate inhibition of apyrase. The control assay signal drops by a factor of 10 in 50 seconds, whilst the assay containing phosphate drops only 10% in this time.

EXPERIMENT 3

Method

1. *Leuconostoc* sp MD 110 was grown by streaking a bead onto de Man Rogosa Sharpe agar to revive bead for stock (place in 30° C. incubator overnight).

1.1. A loop was taken from this plate and transferred to 10 ml Tryptone Soya Broth and grown at 30° C. for exactly 40 hours.

1.2. Once cloudy, indicating that the cells were in early stationary phase, the culture was placed in a place in fridge for 2 hours. Cells were washed twice in ice-cold Reverse Osmosis water in centrifuge (4500 rpm for 10 mins), resuspended in 10 ml cold Reverse Osmosis water and stored in the fridge.

1.3. Cells for the experiment were prepared using a 100× dilution of this stock with a sterile solution of glucose (10 g/l) and $MgCl_2$ (5 mM) at room temperature. Cells were diluted into this solution at least 20 minutes prior to starting each experiment to allow adaptation to the new conditions.

1.4. A special luciferase/luciferin reagent formulated with a detergent-resistant luciferase (Promega, Ultraglo) enzyme was prepared. This was reconstituted in 17.5 ml of 30 mM phosphate /10 g/l a solution of long chain fatty acid ethoxylates.

2. 1 ml of the above cell suspension was added to a cuvette.

3. The suspension was then treated with 1 ml of reconstituted apyrase 0.96 units per ml, and 10 µl of ATP ($10^{-7}$M) was added and left for 15 minutes at room temperature.

4. Two 100 µl aliquots of the treated suspension was transferred to clean cuvettes.

5. To these two cuvettes 100 µl of the luciferase/luciferin reagent formulated with a detergent-resistant luciferase (Promega, Ultraglo) Ultraglo/phosphate/solution of long chain fatty acid ethoxylates was added.

6. After 5 minutes extraction time Cuvette 1 was read in a luminometer.

7. Cuvette 1 was removed from the luminometer and 10 µl of $10^{-7}$M ATP was added to standardise.

8. The sample was returned to the luminometer and read again, then read 5 consecutive times in a row in order to determine the final kinetics of the reaction.

9. After a further five minutes the second water cuvette was read in a luminometer.

10. Steps 7-11 were repeated for cuvette 2.

11. For the control, steps 4 to 13 were repeated but using a luciferase/luciferin reagent formulated with a detergent-resistant luciferase (Promega, Ultraglo) made by reconstituting in 25 mM HEPES buffer pH 7.75 with a solution of long chain fatty acid ethoxylates (10 g/l).

The RLU signal for the assay carried out using a luciferase/luciferin reagent formulated with a detergent-resistant luciferase (Promega, Ultraglo)/phosphate/solution of long chain fatty acid ethoxylates is actually 57% higher at T=10 than at T=5. The RLU signal for the assay that does not contain phosphate (a luciferase/luciferin reagent formulated with a detergent-resistant luciferase (Promega, Ultraglo)/HEPES/solution of long chain fatty acid ethoxylates) is 15% lower at T=10 than at T=5 (FIG. 1).

The amount of ATP (picomole) per assay is 42% higher at T=10 than at T=5 for the assay that contained phosphate (0.0074 picomoles at T=10 compared to 0.0052 picomoles at T=5). The amount of ATP drops by 14% from T=5 to T=10 when the assay does not contain phosphate (0.0016 picomoles at T=5 down to 0.0014 picomoles at T=10) (FIG. 2).

The kinetics of the luciferase/luciferin reagent formulated with a detergent-resistant luciferase (Promega, Ultraglo)/phosphate/solution of long chain fatty acid ethoxylates assay are much more stable than the kinetics of the luciferase/luciferin reagent formulated with a detergent-resistant luciferase (Promega, Ultraglo)/HEPES/solution of long chain fatty acid ethoxylates assay (FIG. 3).

The RLU values for the luciferase/luciferin reagent formulated with a detergent-resistant luciferase (Promega, Ultraglo)/HEPES/solution of long chain fatty acid ethoxylates assay dropped by 97.4% in 75 seconds, whilst the luciferase/luciferin reagent formulated with a detergent-resistant luciferase (Promega, Ultraglo)/phosphate/solution of long chain fatty acid ethoxylates assay RLU values increased by 13% in this time.

EXPERIMENT 4

Method

1. *Leuconostoc* sp MD 110 was grown by streaking a bead onto de Man Rogosa Sharpe agar to revive bead for stock (place in 30° C. incubator overnight).

1.1 A loop was taken from this plate and transferred to 10 ml Tryptone Soya Broth and grown at 30° C. for exactly 40 hours.

1.2. Once cloudy, indicating that the cells were in early stationary phase, the culture was placed in a place in fridge for 2 hours. Cells were washed twice in ice-cold RO water in centrifuge (4500 rpm for 10 mins), resuspended in 10 ml cold Reverse Osmosis water and stored in the fridge.

1.3. Cells for the experiment were prepared using a 100× dilution of this stock with a sterile solution of glucose (10 g/l) and $MgCl_2$ (5 mM) at room temperature. Cells were diluted into this solution at least 20 minutes prior to starting each experiment to allow adaptation to the new conditions.

1.4. 1 ml of the above cell suspension was added to a cuvette.

2. The suspension was then treated with 1 ml of reconstituted apyrase 0.96 units per ml, and 10 µl of ATP ($10^{-7}$M) was added and left for 15 minutes at room temperature.

3. 2×100 µl aliquots of the treated suspension were added to clean cuvettes.

4. To these 2 cuvettes 20 µl of 100 µM pH 7.75 phosphate solution was added.

5. 100 µl of the extractant (a solution of long chain fatty acid ethoxylates) was added and a timer started.

6. After 5 minutes extraction time Cuvette 1 was read in a luminometer.

7. Cuvette 1 was removed from the luminometer and 10 µl of $10^{-7}$M ATP was added to standardise.

8. The sample was returned to the luminometer and read again, then read 5 consecutive times in a row in order to determine the final kinetics of the reaction.

9. After a further five minutes the second water cuvette was read in a luminometer.

10. Steps 7-11 were repeated for cuvette 2.

11. For the control, steps 4 to 13 were repeated but using 20 µl of Reverse Osmosis water in place of 20 µl phosphate.

In the assay that contained the phosphate 100% of the RLU produced after 5 minutes extraction remained 5 minutes later.

In the assay that did not contain phosphate only 31.25% of the RLU signal produced after 5 minutes remained at 10 minutes. (FIG. 4.1)

The results indicate that the phosphate does inhibit apyrase and reduce the amount of ATP broken down in 5 minutes. (FIG. 4.2)

The results also indicate that the level of ATP present in the assay containing phosphate has in fact increased. The high value seen in the second assay is believed to be artifact of the way the amount of ATP per assay is calculated, by the following formula:

(Activity of sample with of ATP standard−activity of sample after ATP extraction)=Amount of ATP (picomole) per assay.

As the light signal produced with an ATP standard is lower at T-10 than at T-5 (believed to be due to the solution of long chain fatty acid ethoxylates damaging the luciferase over time) then the RLU value produced from the ATP extracted from the cells is divisible by a smaller amount. This effect, combined with a slightly higher than expected RLU value at T-10, appears as an increase in the amount of ATP.

The Kinetics for the assays again indicate that phosphate inhibition of apyrase. The control assay RLUs drop by around 12,000 RLU in 46 seconds, whilst the RLU values of the assay containing phosphate drop by around 1,400 RLU in this period.

The graphs shown indicate that phosphate inhibits the action of apyrase. This has the surprising technical effect of providing a method that can be used for analysing the levels of viable cell biomass. After removal of extracellular ATP, the reaction is stopped by the phosphate containing material so that ATP levels which are present due to viable cell biomass can then be used to measure the levels of microorganisms in a sample. There is a stage of removal of extracellular material followed by a stage in which this removal activity is halted so a more accurate indication of the levels of viable cell biomass can be achieved.

The addition of a 5-minute extraction period is beneficial because the solution of long chain fatty acid ethoxylates appears to be quite slow at extracting ATP in the conditions present in these assays. During the five minutes, ATP that is to be extracted can still be broken down by the apyrase but the presence of the phosphate minimizes this effect. This can be seen by the control assay where there is no phosphate inhibition of apyrase, and the poor signal produced by the control assay.

The invention is intended to cover not only individual embodiments or aspects of the invention but also combination thereof. Further, it would be clear to a person skilled in the art that the invention covers all equivalents to the specific embodiments as covered by the claims.

The invention claimed is:

1. An assay method for the detection of viable microbial cells in a sample, the assay method comprising the steps of:

i) isolating a sample containing viable microbial cells having intracellular ATP and extraneous material containing extracellular ATP;

ii) adding an apyrase to the sample to degrade extracellular ATP in the sample;

iii) inhibiting the action of the apyrase enzyme by adding a compound selected from the group consisting of sodium phosphate, potassium phosphate, sodium pyrophosphate, penta-sodium triphosphate, sodium polyphosphate, and combinations thereof; and iv) subjecting the sample to a detection assay to measure the level of undegraded ATP in the sample to provide an indication of the level of viable microbial cells in the sample.

2. An assay method according to claim 1, wherein an extractant is added to the sample prior to assaying the level of undegraded ATP to extract the undegraded ATP from the sample.

3. An assay method according to claim 2, wherein the extractant is a surface-active agent that is used to extract ATP from live cells.

4. An assay method according to claim 3, wherein the surface-active agents include a compound selected from the group consisting of quaternary ammonium compounds, dialkyl ammonium salts, bis-biguanides, and combinations thereof.

5. An assay method according to claim 3, wherein the extractants are used at a concentration of between 0.05-50 g/l.

6. An assay method according to claim 5, wherein the extractant is allowed to react for a period of between 3-10 minutes.

7. An assay method according to claim 2, wherein the extractant is selected from the group consisting of N-N-dimethyldodecan-1-amine, chloroprozamine, and combinations thereof.

8. An assay method according to claim 2, wherein neutralizing agents are added to the sample containing the extractant.

9. An assay method according to claim 2, wherein one or more phosphate-containing materials are added to the sample after the apyrase reaction.

10. An assay method according to claim 1, wherein the apyrase is buffered to have a pH value in the range selected from 9 to 5.

11. An assay method according to claim 1 wherein the assay method is carried out at room temperature, wherein steps ii through iv are completed in a time between 1-30 minutes.

12. An assay method according to claim 1, wherein divalent cations are added with the apyrase.

13. An assay method according to claim 12, wherein the divalent cations are calcium ions and/or magnesium ions.

14. An assay method according to claim 1, wherein a reagent is added to the sample, said reagent being able to enhance levels of ATP in the sample by either increasing intracellular ATP levels by manipulation of cellular metabolism, or by enhancing the activity of luciferase and luciferin to detect ATP.

15. An assay method according to claim 14, wherein the reagent is selected from the group consisting of sodium phosphate, potassium phosphate, ammonium dihydrogen phosphate, penta-sodium triphosphate, sodium polyphosphate, and combinations thereof.

16. An assay according to claim 1, wherein the detection assay is a light emitting assay.

\* \* \* \* \*